(12) United States Patent
Karthikeyan et al.

(10) Patent No.: US 10,467,068 B2
(45) Date of Patent: Nov. 5, 2019

(54) AUTOMATED REMOTE COMPUTING METHOD AND SYSTEM BY EMAIL PLATFORM FOR MOLECULAR ANALYSIS

(71) Applicant: COUNCIL OF SCIENTIFIC AND INDUSTRIAL RESEARCH, New Delhi (IN)

(72) Inventors: Muthukumarasamy Karthikeyan, Pune Maharashtra (IN); Renu Vyas, Pune Maharashtra (IN)

(73) Assignee: Council of Scientific and Industrial Research, Delhi (IN)

( * ) Notice: Subject to any disclaimer, the term of this patent is extended or adjusted under 35 U.S.C. 154(b) by 0 days.

(21) Appl. No.: 15/772,518

(22) PCT Filed: Oct. 28, 2016

(86) PCT No.: PCT/IN2016/050367
§ 371 (c)(1),
(2) Date: Apr. 30, 2018

(87) PCT Pub. No.: WO2017/072794
PCT Pub. Date: May 4, 2017

(65) Prior Publication Data
US 2019/0079812 A1 Mar. 14, 2019

(30) Foreign Application Priority Data
Oct. 30, 2015 (IN) .......................... 3527/DEL/2015

(51) Int. Cl.
*G06F 9/54* (2006.01)
*G06F 9/445* (2018.01)
(Continued)

(52) U.S. Cl.
CPC .............. *G06F 9/543* (2013.01); *G06F 9/445* (2013.01); *G06F 9/4451* (2013.01);
(Continued)

(58) Field of Classification Search
CPC .. G06F 17/2785; G06F 9/4843; G06F 9/4856; G06F 9/4881; G16B 15/00; G16C 10/00; G16C 20/50; G16C 20/90; G16C 99/00
See application file for complete search history.

(56) References Cited

U.S. PATENT DOCUMENTS 5,859,972 A * 1/1999 Subramaniam ....... G06F 16/258
709/203
7,321,437 B2 1/2008 Parry
(Continued)

OTHER PUBLICATIONS

PCT International Search Report and Written Opinion of the International Searching Authority for PCT/IN2016/050367, dated Mar. 30, 2017, 12 pgs.
(Continued)

*Primary Examiner* — Shean Tokuta
(74) *Attorney, Agent, or Firm* — Patterson Thuente Pedersen, P.A.

(57) ABSTRACT

An automated method for remote computing of molecular docking and dynamics from one or more jobs in a network of plurality of users. The invention employs a system to execute the method comprising at least one user device, a remote computing server and a remote database. The job defining action tags are received and scanned by the remote server. A semantic analysis is performed on the jobs to distinguish between customized and non-customized tasks. A data analysis of the jobs is packaged in a compressed format. The user is continually updated of the job status. A public link is generated and sent to the user to download the results. The link is disabled after the downloading of the results to ensure the security of the data. The method avoids any duplication of jobs and can be performed even when the user is offline.

10 Claims, 7 Drawing Sheets

(51) Int. Cl.
| | |
|---|---|
| G06F 9/48 | (2006.01) |
| G16B 15/00 | (2019.01) |
| G16C 99/00 | (2019.01) |
| G16C 20/90 | (2019.01) |
| G16C 10/00 | (2019.01) |
| G06F 17/27 | (2006.01) |
| G06Q 10/10 | (2012.01) |
| G16C 20/50 | (2019.01) |

(52) U.S. Cl.
CPC .......... G06F 9/4843 (2013.01); G06F 9/4856 (2013.01); G06F 9/4881 (2013.01); G06F 9/54 (2013.01); G06F 17/2785 (2013.01); G06Q 10/107 (2013.01); G16B 15/00 (2019.02); G16C 10/00 (2019.02); G16C 20/90 (2019.02); G16C 99/00 (2019.02); G16C 20/50 (2019.02)

(56) References Cited

U.S. PATENT DOCUMENTS

| | | |
|---|---|---|
| 8,660,968 B2 | 2/2014 | Russak |
| 8,873,815 B2 | 10/2014 | Ohnemus |
| 9,183,347 B1 * | 11/2015 | Paxson .................... G16B 5/00 |
| 2004/0019432 A1 | 1/2004 | Sawafta et al. |
| 2006/0132489 A1 | 6/2006 | Blaho |
| 2015/0263900 A1 * | 9/2015 | Polyakov ................ H04L 67/10 709/203 |
| 2016/0277330 A1 * | 9/2016 | Jawaharlal ............. H04L 51/08 |
| 2017/0177411 A1 * | 6/2017 | Thomas ................ G06F 9/5027 |
| 2017/0193349 A1 * | 7/2017 | Jothilingam ........... G06N 3/006 |
| 2019/0079812 A1 * | 3/2019 | Karthikeyan ........... G06F 9/445 |

OTHER PUBLICATIONS

Alessandro Costantini et al: "Porting of GROMACS Package into the Grid Environment: Testing of a New Distribution Strategy", Computational Science and Its Applications—ICCSA 2010, Springer Berlin Heidelberg, Berlin, Heidelberg, vol. 6019, Mar. 23, 2010 (Mar. 23, 2010), pp. 41-52, XP019139586, ISBN: 978-3-642-12188-3.

David E Shaw et al: "Anton, a special-purpose machine for molecular dynamics simulation", Communications of the ACM, Association for Computing Machinery, Inc, United States, vol. 51, No. 7, Jul. 1, 2008 (Jul. 1, 2008), pp. 91-97, XP058236970, ISSN: 0001-0782, DOI: 10.1145/1364782.1364802.

* cited by examiner

```
+------------------------------------------------------------+
| NVIDIA-SMI 352.79    Driver Version: 352.79                |
|-------------------------------+----------------------+-----+
| GPU  Name      Persistence-M| Bus-Id        Disp.A | Volatile Uncorr. ECC |
| Fan  Temp  Perf  Pwr:Usage/Cap|       Memory-Usage | GPU-Util  Compute M. |
|===============================+======================+=====|
|   0  Tesla K80        Off  | 0000:83:00.0     Off |                   0 |
| N/A   47C    P0   125W / 149W |   696MiB / 11519MiB |     99%      Default |
+-------------------------------+----------------------+-----+
|   1  Tesla K80        Off  | 0000:84:00.0     Off |                   0 |
| N/A   36C    P0   136W / 149W |   873MiB / 11519MiB |     99%      Default |
+-------------------------------+----------------------+-----+
|   2  Tesla K80        Off  | 0000:8A:00.0     Off |                   0 |
| N/A   50C    P0   128W / 149W |   898MiB / 11519MiB |     99%      Default |
+-------------------------------+----------------------+-----+
|   3  Tesla K80        Off  | 0000:8B:00.0     Off |                   0 |
| N/A   43C    P0   143W / 149W |   898MiB / 11519MiB |     99%      Default |
+-------------------------------+----------------------+-----+

+------------------------------------------------------------+
| Processes:                                       GPU Memory |
|  GPU       PID  Type  Process name               Usage      |
|============================================================|
|    0     12240    C   ./cudasw                    837MiB    |
|    1     12240    C   ./cudasw                    815MiB    |
|    2     12240    C   ./cudasw                    837MiB    |
|    3     12240    C   ./cudasw                    837MiB    |
+------------------------------------------------------------+
```

Fig. 7

AUTOMATED REMOTE COMPUTING METHOD AND SYSTEM BY EMAIL PLATFORM FOR MOLECULAR ANALYSIS

RELATED APPLICATIONS

The present application is a National Phase entry of PCT Application No. PCT/IN2016/050367, filed Oct. 28, 2016, which claims priority from IN Patent Application No. 3527/DEL/2015, filed Oct. 30, 2015, each of which is hereby fully incorporated herein by reference.

FIELD OF THE INVENTION

The present invention is directed to an automated method and system for job or task processing through electronic mail messages. More particularly, the present invention relates to an automated method and remote computing system to perform molecular docking and dynamics using an electronic message platform.

BACKGROUND AND PRIOR ART OF THE INVENTION

In the age of remote or cloud computing and wearable devices, technology and scientific research drive each other. For instance gadgets such as the wearable computer, which include watch, band and Google Glass® wearable technology, changed the way people use technology. The important aspect of the changing technology is the ability to perform remote computing tasks. For example, transmitting and storing data representing a print job using an e-mail message has been discussed in U.S. Pat. No. 7,321,437. The print jobs are sent as email attachments which are received at the print facility at the remote location which is email enabled. The embodiment in U.S. '437 specifies the job queuing and retention in the memory, extraction of attached documents and the distribution of print jobs to the network printer. Although U.S. '437 discloses the idea of print jobs sent over network, it does not specify the action tags as mails or email subject lines.

Similarly, complex computational chemistry problems can be solved by sending jobs over the network. Researchers working with computational chemistry or any molecular informatics area may have many options for individual or batch job submission either non-interactively or interactively, in case of shell scripts it can be through a pbs script via the command "qsub" included in the script or "<qsub>space<pbs directives>" on the console. Alternately, a user can use portal systems or web browsers to submit jobs with facilities providing web servers, which may or may not provide application programming interface for automation. In this case, a web portal may act as an intermediary between those seeking to submit jobs and the system which actually executes the jobs. The system which opts for monitoring the jobs may provide access to the user to check job status. However the above mentioned method involves a significant amount of technical expertise on the user part. These many options to submit jobs for chemical or biological computing remotely are due to the dire need of heavy computational resources, which usually is, but not limited to, a part of an institutional infrastructure shared by many research groups simultaneously. The user thus has a natural preference for such high performance clusters over their modest desktop machines.

In continuation of the aforesaid problems, in the area of molecular dynamics studies, the researcher routinely has to provide binary files with the coordinates and structure files as an input to the system, as part of computationally intensive jobs. Generating energy trajectory files of macromolecules in a biological system is a computationally intensive job. The minimization and production job is run in multiple binary files containing the input files. The trajectory file obtained at the end of the production run is helpful for understanding the energetics of a protein model in a dynamic system.

In the area of chemical informatics, wherein the researcher submits input molecules in any standard chemical data exchange formats, for virtual library generation, has to go through a pipeline or an array of specific computational chemistry steps such as scaffold extraction, the subcomponents of which are compound fragments, eventually participate in a combinatorial virtual reaction to arrive at a final chemical virtual library.

US 2004/0019432 discusses a method for integrating a computer-aided molecular discovery process across a plurality of computer-aided molecular discovery applications, wherein the sequence or structure of the protein is retrieved, binding sites identified, and compounds are docked in a heterogeneous cluster. However, there has been no mention of an elastic cloud computing system when the load is high and the remote computing scenario has not even been discussed.

US 2006/0132489 refers to a graphical processor coupled with the normal processor to share the overload of the remote computing jobs such as image compression, decompression and image processing. But the invention claimed in US2006/0132489 does not highlight the method or apparatus for transmission of messages and receiving data as remote jobs and response executed on remote systems.

Further, U.S. Pat. No. 8,660,968 (Indian equivalent 1964/MUMNP/2013) relates to systems and methods for remote classification of chemical reaction assays.

Furthermore, U.S. Pat. No. 8,873,815 discloses a method and apparatus for the remote analysis of a chemical compound microarray supported on a substrate and is adapted to enable a user, such as medical personnel, to access the diagnostic functions by sending an image to the remote server via an e-mail, web portal, or mms text message. The pixels in the [said] image are compared to the reference pixels. The image analysis application alters the image in order to calibrate the pixels of the image to correlate to the properties of the reference pixels. The image application is further configured to inspect/analyze the pixels in the image, and identify those colors within a gradient range of the calibrated pixels. The image application then compares the pixel values with values stored within the database or the memory store. The stored values can correspond to a particular illness, while the intensity of the colors of the image can correspond to the severity of the infection, deficiency, or status.

It is a point to be noted that all of the aforementioned prior arts refer to client-server design where the user needs to be connected to the system to send and receive the data. None of the cited documents discusses the offline processing of the jobs.

In view of stated specific task of performance under high load, the inventors of present invention suggests a novel way of sending text data or structure data by e-mail to a host computer and evaluate the data.

The present invention is a comprehensive and well defined resource of remote job submission for chemical computing.

OBJECTS OF THE INVENTION

The present invention simplifies the job submission and data retrieval process for chemical computing, drug design and discovery using a remote and cloud computing system.

Another objective is to use email as the main source of information exchange (synchronous/asynchronous mode) which aids in job submission over the network to access any remote and cloud computing services.

SUMMARY OF THE INVENTION

The present invention discloses an automated method for remote computing of molecular docking & dynamics from one or more jobs in a network of a plurality of users. The method employs a remote computing system comprising at least one user device, a remote server and a remote computing database.

In an aspect, the method comprises the following steps:
- sending at least one job/input from a remote location from at least one user device to the remote server, each job/input defining one or more action tags;
- tracking the job by a job tracker of the remote server;
- feeding the jobs to a job analyzer by a job feeder of the remote server;
- receiving and scanning the jobs accumulated in the remote server by a job scanner of the remote server;
- performing a semantic analysis of the action tags contained with the jobs by a job analyzer of the remote server;
- distinguishing between customized and non-customized tasks defined in the action tags by the job analyzer;
- expanding the action tags in a job preparation phase by the job analyzer, the job preparation phase includes cavity prediction and extracting active site center co-ordinates from a predefined list of a remote computing database;
- transforming the job preparation phase into a job render phase;
- transforming the render phase into an action phase, wherein the action phase includes triggering the remote computing system into action and running the jobs with continuous monitoring for updating the user via e-mail by a job runner of the remote server;
- packaging a data analysis in a standard compressed format by the job analyzer;
- updating status using email messages back to the user by email and providing a hyperlink to central repository with authentication;
- retrieving the results and a mode of its delivery to the user by sending the status of the job and availability of data;
- uploading the resultant data to any backup space server, a file server, a data server or a cloud server in a compressed and an encrypted format;
- generating a public link for download of results, wherein the link is sent to the user over the network via email and
- disabling the downloaded link after a specific time interval or a first download event to enhance data access security.

By employing the method, duplication of jobs is avoided. Further, the method may be implemented even during offline status of the user/s.

In another aspect of the invention, the molecules are converted from 2D to 3D by the job runner. However when only the chemical names are submitted for the job, corresponding 2D and 3D structures are generated automatically by the job runner.

In yet another aspect of the invention, the user is provided with the flexibility to submit jobs and retrieve data or results on the fly without technical expertise.

In yet another aspect of the invention, the workflow is fully automated, and measured against a time performance analysis.

Further, the method of the present invention supports the utilization of remote computational resources including Graphical Processing Units (GPU) capable of performing parallel calculations extremely faster. The email message can be configured to utilize the available GPU processors for parallel jobs.

BRIEF DESCRIPTION OF THE DRAWINGS

FIG. 7 analyzer the complete utilization of available GPU processors while performing the remote computing task.

DETAILED DESCRIPTION OF THE INVENTION

Figure 1:
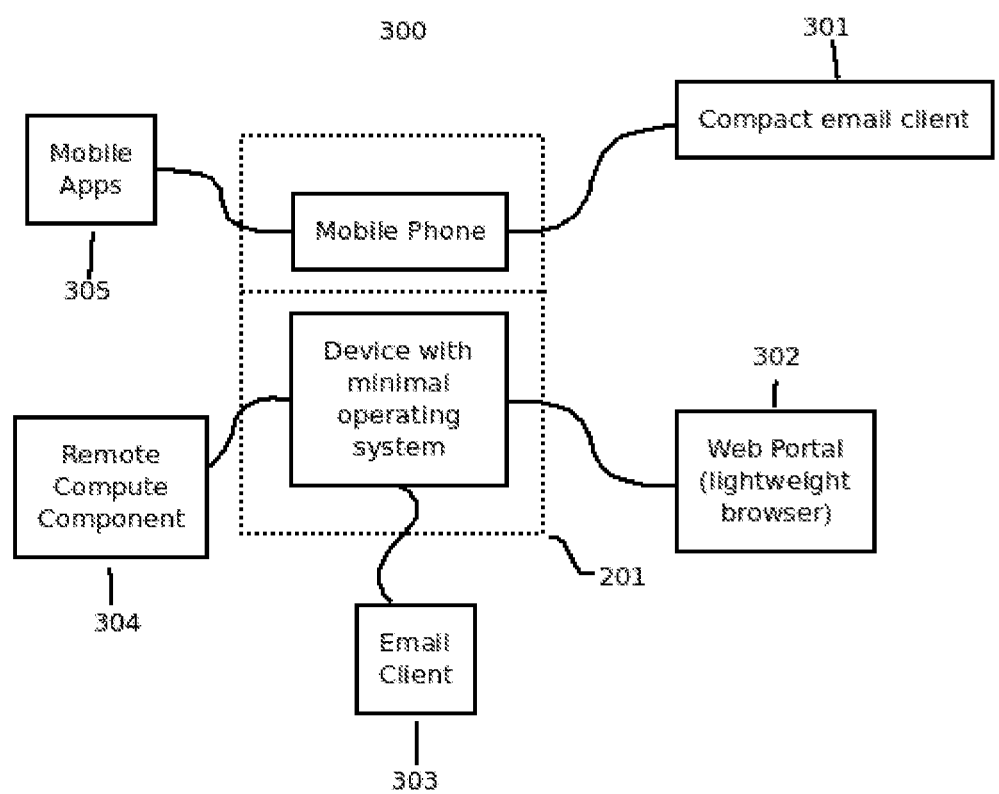
FIG. 1 depicts a device to submit and receive data to and from remote computing servers.

A method of the present invention facilitates submitting jobs, preferably molecular data, over the network as short email messages and provides a way to trigger molecular docking, molecular dynamics or molecular discovery tasks, to be computed in a remote computing platform, leveraging distributed and cloud computing scales, transmitting jobs as emails or short messages.

The email track manager tracks the status of the job, from the moment the job is received by the job receiver, read by the job collector, analyzed by the job analyzer till the point at which the job either completes or fails.

The system herein accepts the pdbqt file of the receptor and performs the cavity prediction to extract x, y, z coordinates of the active site center and finally the docking is completed with the final selection of the most favorable pose for elucidation of any therapeutic activity.

The jobs are accumulated use-wise or task-wise and the job scheduler processes them at regular intervals of time. Once the email is read and scanned, it is marked as READ and is not visited again, avoiding duplication of job run. Semantic analysis of plain email subjects is performed by the job analyzer to interpret action tags.

The method further distinguishes between customized and non-customized tasks. The non-customized tasks are run by default system job cards where as customized tasks need creation of job cards dynamically and at times may require manual interference by the user to abort the job and start afresh with job refinement and refined job cards.

If the job card is created for docking, and if the action tag specifies compound class, the expansion strategy involves querying and collecting all the compounds from the remote computer database.

The method of the present invention creates a job card, after email subject line parsing, and after the approval of job analyzer. The information in the job card is automatically filled using the parameter feed by the job analyzer to update the user. The user may then abort the job through email or may go for abort and resubmit job with refinement.

With the use of the present invention, the user can send short messages for performing complex tasks such as docking, virtual screening or molecular dynamics; receiving jobs in subject lines, main email body or as an attachment as emails.

For example, if a simple subject line such as "aspirin_10gs" docks protein with pdbid 10gs against the compound with name aspirin is submitted, the method of the present invention converts the chemical name to standard chemical structure formats such as mol2 or sdf.

The text mining process may comprise data pre-processing, such as natural language processing followed by named entity recognition of chemical and biological entities mentioned above, wherein any predictive modeling, supervised, unsupervised or hybrid can be used for extraction and deep learning protocols.

The specification describes the action tag specification for subject line management when the jobs are submitted via emails. The action tag specification or job submission protocol is a tag based markup language which is used to describe the input parameters or the data or the subject line for job submission. It details on the central remote job management infrastructure and elucidates the type of response raised by the remote computing for handling any type of tasks related to computational chemistry or bioinformatics, e.g. virtual screening or text mining. The response is timed based on the job status, and it is immediate if the job fails due to non-compliance with the action tagging specification or protocol. The decision making component is based on action tags and it initiates to make a choice between the remote standalone or remote cloud system. Also the system, wherein the software includes the use of creating, configuring the virtual machines can be scaled up and down sensing the load at any given point of time. The system utilizes the virtualization technology to bring up as many nodes required without having the need to specify it by the user. The system configures all the network interfaces between these virtual machines for communication and completion of the tasks given.

The user may have the option of not leaving any trail of the job, including the submission, data input, logs, job statistics and output, wherein the system should create an exception to the record keeping rule for maintaining the security of the request.

The method of the present invention encodes molecules or compounds belonging to a particular class such as, but not limited to a therapeutic category such as anti-convulsion, anti-neoplastic, anti-analgesic etc. or any natural compound classes such as flavonoids, alkaloids, steroids, glycosides, lignans, polyketides, saponins, terpenes etc. with the required action fingerprint.

The job thus submitted may be a text mining job for diseases such as, but not limited to, malaria, cancer, diabetes, tuberculosis, etc. to extract named chemical or biological entities. The biological entities may include, but are not limited to, protein molecules, genes, DNA, RNA, peptides, organic compounds, related disease names, viral components, cell components, cell line or cell type, protein complex, tissue etc.

The different classes thus obtained can be subjected to a frequency based analysis on different parameters such as document similarity or semantics for determination of contacts between them. The contacts thus established may reveal hidden relationships between them never evident before due to the often isolated nature of any scientific work. The contacts thus highlighted can be visualized in the form of a classical network with entities defining nodes and edges symbolizing the relation; further various parameters such as edge width or color coding based on confidence scores can be adopted to enhance the network for knowledge discovery.

As shown in FIG. 1, a device (201) is shown to submit and receive data to and from remote computing servers. The device (201) may be any communication device which can host the minimal operating system with the least amount of resources, such as, but not limited to, the Raspberry Pi® device, a popular device for experimental work and for hardware enthusiasts, or a mobile device which can run applications such as email client programs (301), or lightweight browsers for using web portals (302) and mobile apps (305). The Raspberry Pi® device has the capacity to lend itself for the scale up to form a private cloud and interestingly, become part of the remote computing services. The device (201) includes a remote computing component (304).

In another embodiment, the component as a whole can be a web portal, a user interface for job submission management and can act as a comprehensive resource to maintain updates and archives received from the remote computing services. The portal will be used as a website but with dynamic features for job submission, large scale data (results) retrieval, job status logs, job archive log etc.

Figure 2:
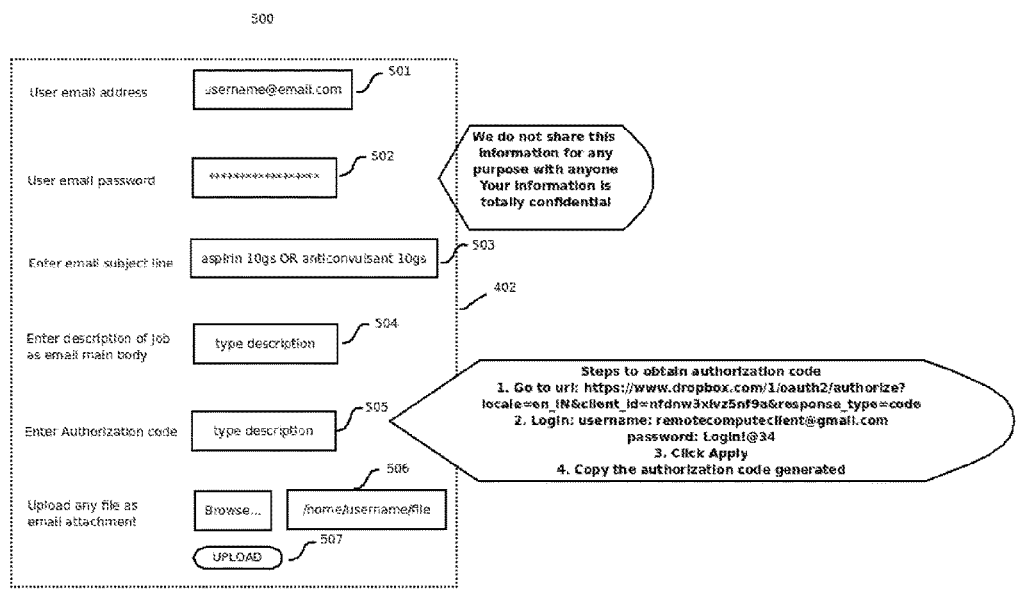
FIG. 2 depicts a screenshot of submission of molecular docking job through email using the web component to the remote computing services in one of the embodiments.

The usage of the job submission module can be completed by supplying basic information on the portal as shown in FIG. 2 such as email address (501), password (502), the actual subject line, job description, authorization code for downloading the results and uploading email attachments if any.

Figure 3:
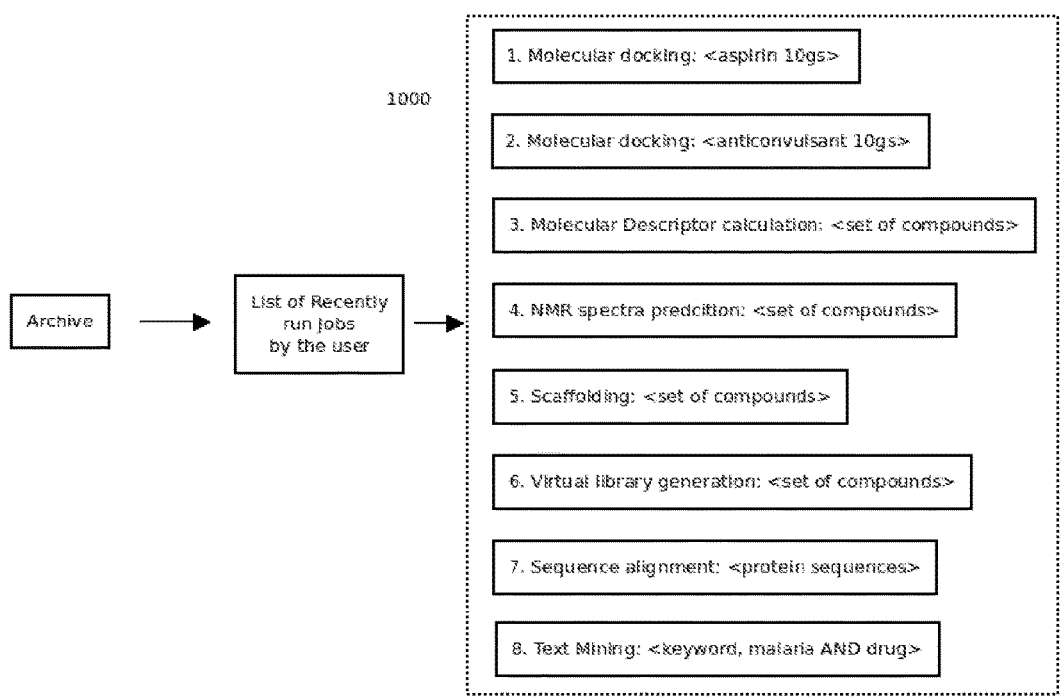
FIG. 3 depicts the list of all the jobs related to the molecular informatics submitted by the user recently.

According to FIG. 3, the remote service system supports individual or bulk molecular docking, molecular descriptors/property calculation, NMR spectra prediction, scaffolding, virtual library generation, protein or nucleotide sequence alignment, text mining etc. The job tracker is initiated as soon as the job arrives in the email INBOX. It starts for instance when the email message is being scanned by a job scanner, when jobs are collected by the job collector, when the job analyzer analyzes the parameters to prepare a job card, or with the job feeder feeding it to the job runner after approval from the user and also when the job is running. This makes up a robust monitoring mechanism at the remote service end with an automated updating feature.

The online email job submission makes submitting jobs simple and in an automated fashion without any manual intervention; the user can get the results pertaining to the molecular discovery process being performed all through the email.

Figure 4:
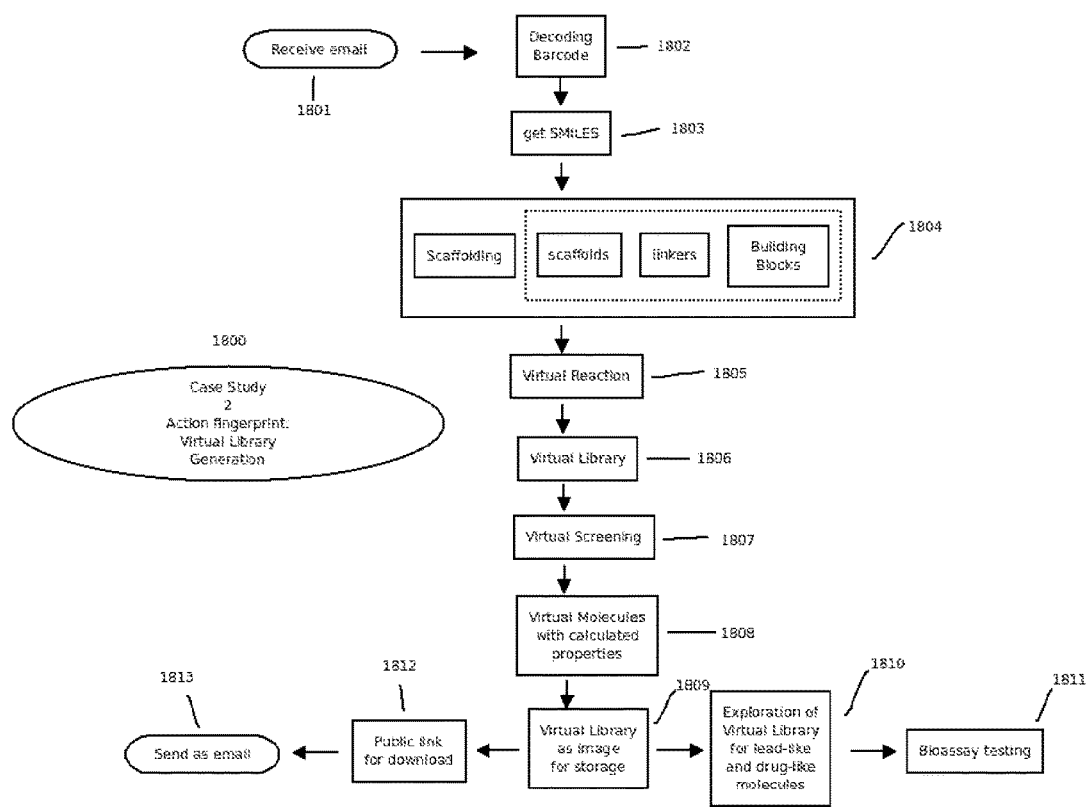
FIG. 4 depicts virtual library generation from the encoded set of input molecules.

FIG. 4 illustrates virtual library generation for the method of the present invention. Referring to FIG. 4, the remote computing system receives an e-mail (1801) from the user. For this embodiment, the molecular structure is encoded (1802) in a barcode. After scaffolding (1804) is carried out, a virtual reaction (1805), a virtual library (1806), a virtual screening (1807) and a virtual molecule with calculated properties (1808) is generated. Followed by this, a virtual library as image for storage (1809) is generated. A public link for downloading of the results is created (1812) and is delivered via an e-mail (1813) to the user.

Figure 5:
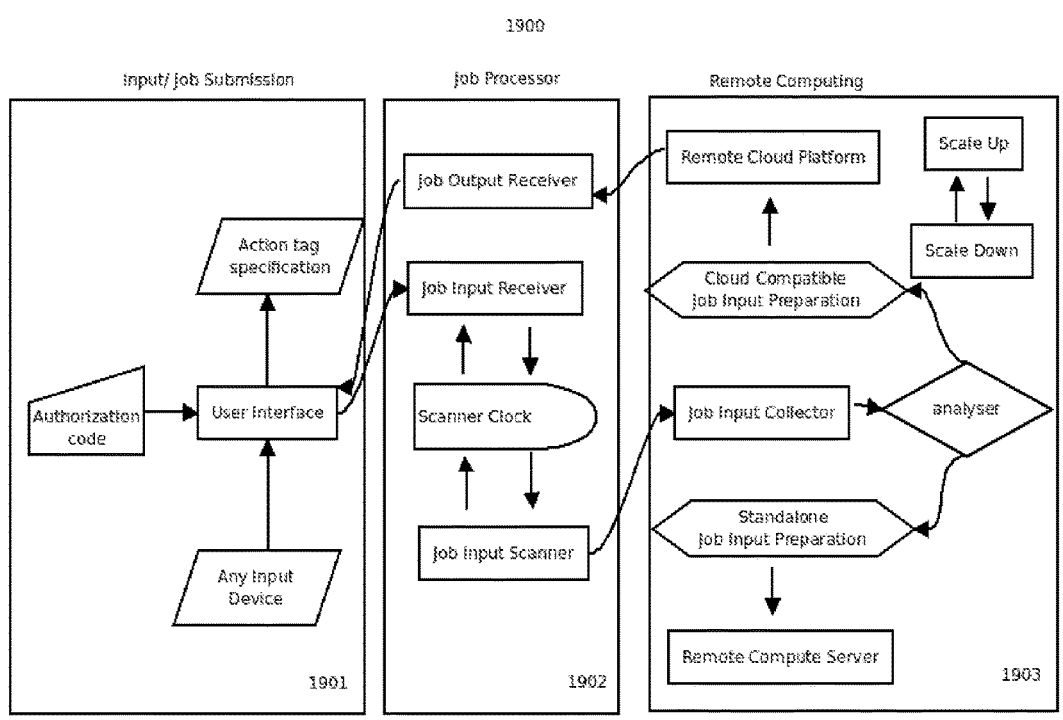
FIG. 5 depicts the overview of the remote computer platform and the overall modular interactivity.
Figure 6:
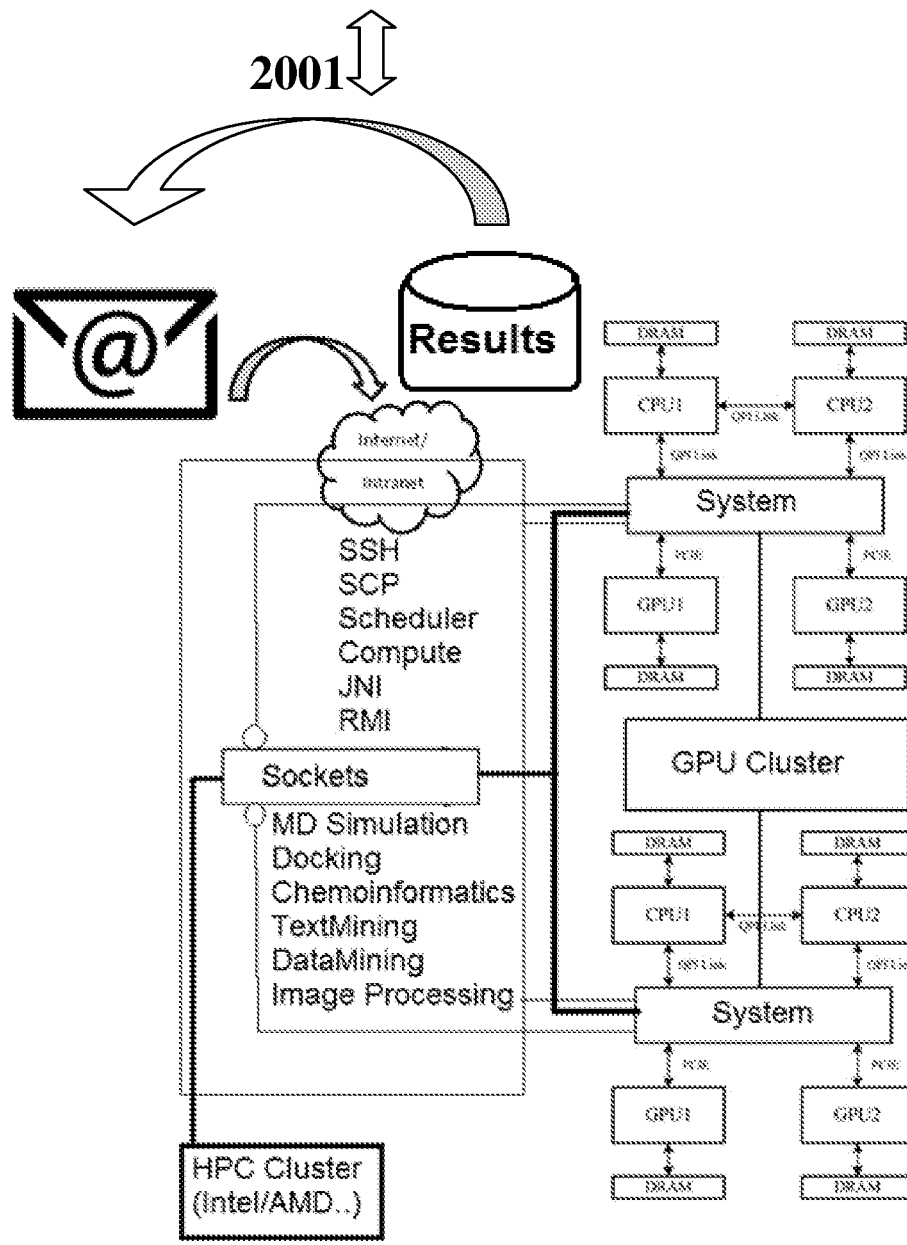
FIG. 6 depicts a block diagram of email compute platform where the email is processed (2000) and types and tasks to be performed with internal communication protocols for the flow of data within the system. The output of the results are stored externally and the links are sent by email (2001).

According to FIG. 5, during the job submission stage (1901), the job is input from any user device. The authentication code is associated with the user input. The job is received by the input receiver in a job processor stage (1902). Simultaneously, the action tag specification is raised in response to the received job. In the job processor stage (1902), the job is scanned by the job scanner and sent to the job input collector of the remote computing stage (1903). The job analyzer analyses the job and if the job is in bulk, then it is sent to the remote cloud platform, which is subsequently sent to the job output receiver of the job processor stage (1902). If the job is a standalone, then it is sent to the remote computing server.

The following examples are given by way of illustration only, and therefore should not be construed to limit the scope of the invention.

Example 1

The data is supplied such as protein data bank ID, Ligand name or Ligand/Compound class name, uploading ligand structures if any, opting for cavity/active site prediction for the receptor molecule or protein, or supplying user defined active site 3D coordinates along with the grid size dimensions. The submission of the data sends an email to the remote server wherein, the message is further deciphered to carry on the required task. The job tracker for the job submit event is automatically allocated which keeps the user updated, through e-mail, after the user subscribes for receiving updates. For this purpose, a repository is created for most of the structures in the Protein Data Bank with their native ligands in the in-house database for ready use. In the case a particular target is not available, it may be downloaded from an online resource and then used for docking. If the user does not specify the active site coordinate, the system uses the internal remote computing database to get those values.

```
SMILES FORMAT [space] PDB_ID
CC(=O)Oc1ccccc1C(=O)O 2jd1
SMILES FORMAT [space] PDB_ID[space] center_x [space]
center_y [space]
center_z [space] grid_x [space] grid_y [space] grid_z
CC(=O)Oc1ccccc1C(=O)O 2jd1 13.1446 6.5503 −7.8722 40 40 40
```

A typical execution of the above request on the remote server is shown as follows:

```
vina/bin/vina --receptor receptor/2jd1/protein.pdbqt --ligand
ligands/ligand.pdbqt --
center_x 13.1446 --center_y 6.5503 --center_z −7.8722 --size_x
40 --size_y 40 --
size_z 40 --cpu 24 --log log_dock.txt --exhaustiveness 2 --num_modes
2 --out
out_dock.txt &
```

1. The results are discussed as the output of the above process is recovered. The output, thus obtained in the following format for the top two bound poses is as shown below

| MODEL 1 | | | | | | | | | |
|---|---|---|---|---|---|---|---|---|---|
| REMARK | VINA | | RESULT: | | −7.1 | | 0.000 | | 0.000 |
| REMARK | | | Name | | | = | | | 451 |
| REMARK | | | x | y | z | vdW | Elec | q | Type |
| REMARK | | | | | | | | | |
| ROOT | | | | | | | | | |
| ATOM | 1 | N | LIG | 1 | 11.231 | 5.142 | −7.692 | 0.00 | 0.00 | −0.200 | N |
| ATOM | 2 | C | LIG | 1 | 11.403 | 4.670 | −6.394 | 0.00 | 0.00 | +0.185 | A |
| ATOM | 3 | N | LIG | 1 | 10.278 | 4.087 | −6.008 | 0.00 | 0.00 | −0.128 | NA |
| ATOM | 4 | N | LIG | 1 | 9.332 | 4.267 | −6.985 | 0.00 | 0.00 | −0.136 | NA |
| ATOM | 5 | C | LIG | 1 | 9.904 | 4.925 | −7.962 | 0.00 | 0.00 | +0.249 | A |
| ENDROOT | | | | | | | | | |
| BRANCH | | | | | 2 | | | | 6 |
| ATOM | 6 | C | LIG | 1 | 12.595 | 4.811 | −5.558 | 0.00 | 0.00 | +0.021 | A |
| ATOM | 7 | C | LIG | 1 | 12.973 | 6.082 | −5.104 | 0.00 | 0.00 | +0.011 | A |
| ATOM | 8 | C | LIG | 1 | 14.109 | 6.243 | −4.307 | 0.00 | 0.00 | +0.001 | A |
| ATOM | 9 | C | LIG | 1 | 14.884 | 5.136 | −3.966 | 0.00 | 0.00 | +0.000 | A |
| ATOM | 10 | C | LIG | 1 | 14.531 | 3.870 | −4.429 | 0.00 | 0.00 | +0.001 | A |
| ATOM | 11 | C | LIG | 1 | 13.395 | 3.707 | −5.226 | 0.00 | 0.00 | +0.011 | A |
| ENDBRANCH | | | | | 2 | | | | 6 |
| BRANCH | | | | | 1 | | | | 13 |
| ATOM | 12 | C | LIG | 1 | 11.858 | 6.969 | −8.857 | 0.00 | 0.00 | +0.133 | C |
| ATOM | 13 | N | LIG | 1 | 12.083 | 5.726 | −8.585 | 0.00 | 0.00 | −0.172 | NA |
| BRANCH | | | | | 12 | | | | 15 |
| ATOM | 14 | C | LIG | 1 | 12.351 | 7.643 | −11.143 | 0.00 | 0.00 | +0.009 | C |
| ATOM | 15 | C | LIG | 1 | 12.689 | 7.684 | −9.848 | 0.00 | 0.00 | +0.022 | C |
| BRANCH | | | | | 14 | | | | 19 |
| ATOM | 16 | C | LIG | 1 | 14.697 | 9.554 | −14.166 | 0.00 | 0.00 | +0.000 | A |
| ATOM | 17 | C | LIG | 1 | 15.089 | 9.598 | −12.830 | 0.00 | 0.00 | +0.001 | A |
| ATOM | 18 | C | LIG | 1 | 14.312 | 8.973 | −11.851 | 0.00 | 0.00 | +0.008 | A |
| ATOM | 19 | C | LIG | 1 | 13.129 | 8.307 | −12.200 | 0.00 | 0.00 | −0.025 | A |
| ATOM | 20 | C | LIG | 1 | 12.755 | 8.254 | −13.551 | 0.00 | 0.00 | +0.008 | A |
| ATOM | 21 | C | LIG | 1 | 13.534 | 8.879 | −14.528 | 0.00 | 0.00 | +0.001 | A |
| ENDBRANCH | | | | | 14 | | | | 19 |
| ENDBRANCH | | | | | 12 | | | | 15 |
| ENDBRANCH | | | | | 1 | | | | 13 |
| TORSDOF | | | | | | | | | 4 |
| ENDMDL | | | | | | | | | |

-continued

MODEL 1

```
MODEL                                                                           2
REMARK    VINA       RESULT:         −7.0            4.171             9.941
REMARK               Name                       =                      451
REMARK               x      y        z      vdW       Elec      q      Type
REMARK
ROOT
ATOM     1  N  LIG  1  11.661   4.568   −5.365   0.00   0.00   −0.200   N
ATOM     2  C  LIG  1  11.530   4.786   −6.733   0.00   0.00   +0.185   A
ATOM     3  N  LIG  1  11.006   5.988   −6.917   0.00   0.00   −0.128   NA
ATOM     4  N  LIG  1  10.684   6.519   −5.694   0.00   0.00   −0.136   NA
ATOM     5  C  LIG  1  11.048   5.648   −4.785   0.00   0.00   +0.249   A
ENDROOT
BRANCH                          2                                       6
ATOM     6  C  LIG  1  11.867   3.854   −7.809   0.00   0.00   +0.021   A
ATOM     7  C  LIG  1  11.657   4.234   −9.142   0.00   0.00   +0.011   A
ATOM     8  C  LIG  1  11.969   3.361  −10.187   0.00   0.00   +0.001   A
ATOM     9  C  LIG  1  12.481   2.095   −9.909   0.00   0.00   +0.000   A
ATOM    10  C  LIG  1  12.674   1.698   −8.587   0.00   0.00   +0.001   A
ATOM    11  C  LIG  1  12.364   2.570   −7.541   0.00   0.00   +0.011   A
ENDBRANCH                       2                                       6
BRANCH                          1                                      13
ATOM    12  C  LIG  1  11.923   3.527   −3.381   0.00   0.00   +0.133   C
ATOM    13  N  LIG  1  12.219   3.554   −4.639   0.00   0.00   −0.172   NA
BRANCH                         12                                      15
ATOM    14  C  LIG  1  12.073   2.393   −1.233   0.00   0.00   +0.009   C
ATOM    15  C  LIG  1  12.512   2.503   −2.493   0.00   0.00   +0.022   C
BRANCH                         14                                      19
ATOM    16  C  LIG  1  13.550  −0.484    1.566   0.00   0.00   +0.000   A
ATOM    17  C  LIG  1  12.245  −0.006    1.662   0.00   0.00   +0.001   A
ATOM    18  C  LIG  1  11.776   0.937    0.743   0.00   0.00   +0.008   A
ATOM    19  C  LIG  1  12.613   1.418   −0.274   0.00   0.00   −0.025   A
ATOM    20  C  LIG  1  13.918   0.915   −0.370   0.00   0.00   +0.008   A
ATOM    21  C  LIG  1  14.385  −0.028    0.549   0.00   0.00   +0.001   A
ENDBRNCH                       14                                      19
ENDBRANCH                      12                                      15
ENDBRANCH                       1                                      13
TORSDOF                                                                 4
ENDMDL
```

The output.txt file of the docking process is completed.

The log file contains the following results for the top two docked poses:

| Pose id | Binding energy (kcal/mol) | RMSD(Lower Bound) | RMSD(Upper Bound) |
|---|---|---|---|
| 1 | −7.1 | 0.000 | 0.000 |
| 2 | −7.0 | 4.171 | 9.941 |

Example 2

In this example, it is demonstrated that the method and system of the present invention can perform tasks such as molecular dynamics, molecular docking, virtual library building and analysis related to drug discovery research. Molecular dynamics was carried out against two proteins Ubiquitin (PDB ID: 1UBQ) and Lysozyme (PDB ID: 1AKI) by employing two existing molecular dynamics tools namely GROMACS and NAMD. The user specifies the PDB ID along with the water model in the email, using any computational device like smartphone, laptop, tablet or like. The email is received by the remote server wherein the message is deciphered to carry out the molecular dynamics tasks. The job is assigned to a tasker program, which allocates the job to any available active virtual machine in cloud implementation. The protein structure is solvated using the water model specified in the message, followed by minimization, equilibration and then the final dynamics step of production run is carried out. The output trajectory files in GROMACS like .xtc, .gro, .trr, .tpr, .cpt, .log and .top or .dcd, .coor and .xtc in NAMD are compressed and sent to the cloud storage or public storage, for example drop box. The link to the drop box location is then mailed to the user after the job completion. The job trackers for the job submit automatically updates to the user through mail or SMS. This method of remote computing using cloud has been demonstrated for running six MD simulations simultaneously on six different systems, thereby saving a considerable amount of time.

The output files and other data obtained is tabulated below:

| Protein | Water Model | Minimization steps | Equilibration (fs) | | Production run (ns) | RMSD (nm) | Energy (Kcal/mol) |
|---|---|---|---|---|---|---|---|
| | | | NVT | NPT | | | |
| 1UBQ | TIP3P | 500 | 1000 | 1000 | 1 | 0.12 | −4.21 |
| 1AKI | TIP3P | 500 | 1000 | 1000 | 1 | 0.82 | −5.61 |

Example 3

Typical sequence search using GPU query is shown below using the cudasw tool in a remote email computing platform.

```
./gpusw -qprf 1 -query Queries/Q9UKN1.fasta -db simdb.fasta -num__threads 8 -num__gpus 4
name:Tesla K80 (x 4 Nos)
multiprocessor count:13
clock rate:823500 MHz
shared memory:49152
global memory:12079136768
registers per block:65536
Compute capability: 3.7
L2 cache size: 1572864
Max Query Length for Query Profile Variant: 1258
Use the first 4 compatible GPUs and 8 CPU thread(s)
/**********************************/
    Scoring matrix:
    Gap Open penalty:        10
    Gap Extension penalty:        2
    QUERY PROFILE will be used
the scoring matrix ( ) can not be found
the default scoring matrix (BLOSUM62) is used
Loading database sequences from file into host memory...
[calcThreshold] 2.4 0.8235 8 52
[calcThreshold]0.877105 3000
overall mean: 3000
mean 3000 deviation 0
Loading database successfully
numSeqs: 200000 numThreshold: 175421
maxSeqLength: 3000 totalAminoAcidsThreshold: 526263000 totalAminoAcids: 600000000
query:gi|187609692|sp|Q9UKN1.2|MUC12__HUMAN RecName: Full=Mucin-12;
Short=MUC-12; AltName: Full=Mucin-11; Short=MUC-11; Flags: Precursor
Length: 5478 --- time: 7.24156 (s) and GCUPS: 453.88 ms
Query-2 using CUDA Platform
Loading database sequences from file into host memory...
[calcThreshold] 2.4 0.8235 8 52
[calcThreshold]0.877105 1352
overall mean: 249
mean 223 deviation 205
Loading database successfully
numSeqs: 62845 numThreshold: 62005
maxSeqLength: 7312 totalAminoAcidsThreshold: 13755784 totalAminoAcids: 15693617
----------Display the top 10 ----------
score: 166 -- Q5URB9 YR840__MIMIV^|^^|^Putative ankyrin repeat protein
R840^|^^|^^|^Acanthamoeba polyphaga mimivirus^|^212035^|^Virus^|^10239
score: 145 -- Q5UPU4 YR267__MIMIV^|^^|^Putative ankyrin repeat protein
R267^|^^|^^|^Acanthamoeba polyphaga mimivirus^|^212035^|^Virus^|^10239
score: 145 -- Q5UQ08 YR787__MIMIV^|^^|^Putative ankyrin repeat protein
R787^|^^|^^|^Acanthamoeba polyphaga mimivirus^|^212035^|^Virus^|^10239
score: 144 -- Q5UPE2 YL063__MIMIV^|^^|^Putative ankyrin repeat protein
L63^|^^|^^|^Acanthamoeba polyphaga mimivirus^|^212035^|^Virus^|^10239
score: 137 -- Q5UPH0 YL100__MIMIV^|^^|^Putative ankyrin repeat protein
L100^|^^|^^|^Acanthamoeba polyphaga mimivirus^|^212035^|^Virus^|^10239
score: 136 -- Q5UQZ7 YR901__MIMIV^|^^|^Putative ankyrin repeat protein
R901^|^^|^^|^Acanthamoeba polyphaga mimivirus^|^212035^|^Virus^|^10239
score: 133 -- Q5UP13 YR846__MIMIV^|^^|^Putative ankyrin repeat protein
R846^|^^|^^|^Acanthamoeba polyphaga mimivirus^|^212035^|^Virus^|^10239
score: 131 -- Q5UP11 YR848__MIMIV^|^^|^Putative ankyrin repeat protein
R848^|^^|^^|^Acanthamoeba polyphaga mimivirus^|^212035^|^Virus^|^10239
score: 129 -- Q5UPR3 YR777__MIMIV^|^^|^Putative ankyrin repeat protein
R777^|^^|^^|^Acanthamoeba polyphaga mimivirus^|^212035^|^Virus^|^10239
score: 129 -- Q5UR04 YR911__MIMIV^|^^|^Putative ankyrin repeat protein
R911^|^^|^^|^Acanthamoeba polyphaga mimivirus^|^212035^|^Virus^|^10239
query:Q38101 Q38101__BPR1T^|^^|^ORF15^|^^|^^|^Lactococcus phage
r1t^|^43685^|^Virus^|^10239
Length: 64 --- time: 0.026444 (s) and GCUPS: 37.9819 ms
```

Results truncated for brevity. This example demonstrates the GPU utilization for sequence searching that is most frequently used in bioinformatics domain for clustering the sequences to classification of species and identify the similar query sequence faster by scanning against millions/billions of target sequences. The complete utilization of available GPU processors is shown in FIG. 7.

The invention can be further extended to any other tasks such as analysis of data using text analytics, for example patient management system, computational law, quality control, tax filing verification or any other related data or relevant domains in a secured and automated environment under human computer interface (HCI). Alternately, the system of the present invention may further be integrated with other deep learning systems including image and video processing, voice-to-voice systems, for example audio to text input systems where the users could use live/interactive voice using a mic or audio capture device or pre-recorded audio file as an attachment to process the job in an automated remote computing environment. The output of computed data in textual format could be transformed into audio data using text to voice conversion routines and transmitted back to the user.

The invention claimed is:

1. An automated method for remote computing of molecular docking and dynamics from one or more jobs in a network of a plurality of users, by employing a remote computing system comprising at least one user device, a remote server and a remote computing database, wherein duplication of jobs is avoided, and wherein said method is implemented even during offline status of the user/s, comprising:

i. sending at least one job/input from a remote location from at least one user device to the remote server, each job/input defining one or more action tags;
ii. tracking the job by a job tracker of said remote server;
iii. feeding the jobs to a job analyzer by a job feeder of said remote server;
iv. receiving and scanning the jobs accumulated in said remote server by a job scanner of said remote server;
v. performing a semantic analysis of the action tags contained with said jobs by a job analyzer of said remote server;
vi. distinguishing between customized and non-customized tasks defined in said action tags by said job a analyzer:
vii. expanding said action tags in a job preparation phase by said job analyzer, said job preparation phase including cavity prediction and extracting active site center co-ordinates from a predefined list of a remote computing database;
ix. transforming said job preparation phase into a job render phase;
x. transforming the render phase into an action phase, wherein said action phase includes triggering said remote computing system into action and running said jobs with continuous monitoring for updating said user via e-mail by a job runner of said remote server;
xi. packaging a data analysis in a standard compressed format by said job analyzer;
xii. updating status using email messages back to the user via email and providing a hyperlink to said remote computing storage system with authentication;
xiii. retrieving the results and a mode of its delivery to the user by sending the status of the job and availability of data;
xiv. uploading the resultant data to any backup space server, a file server, a data server or a cloud server in a compressed and an encrypted format;
xv. generating a public link for download of results, wherein said link is sent to the user over the network via email; and
xvi. disabling said downloaded link after a specific time interval or a first download event to enhance data access security.

2. The method according to claim 1, wherein said jobs are accumulated use-wise or task-wise.

3. The method according to claim 1, wherein non customized tasks are run by default system job cards and said job cards are created dynamically for customized tasks.

4. The method according to claim 1, wherein job cards are created by manual interference of the user for customized tasks.

5. The method according to claim 4, wherein job cards are created for customized tasks by aborting jobs cards created by said non customized tasks and starting afresh with job refinement.

6. The method according to claim 1, wherein molecules or compounds belonging to a particular class including, but not limited to a therapeutic category as anti-convulsion, anti-neoplastic, anti-analgesic and any natural compound classes such as flavonoids, alkaloids, steroids, glycosides, lignans, polyketides, saponins, terpenes with the required action fingerprint are encoded in said remote database.

7. The method according to claim 1, wherein said job may be text mining or molecule docking for calculating binding energy of chemical and biological entities and a class of compounds selected from protein molecules.

8. The method according to claim 7, wherein the text mining process comprises of data pre-processing, natural language processing followed by named entity recognition of chemical and biological entities; and wherein any predictive modeling, supervised, unsupervised or hybrid can be used for extraction.

9. A system to execute the said method as claimed in 1 comprising one user device, a remote computing server and a remote database wherein said remote computing system is a single node or a cluster of nodes or a multi-node and multi-instance cloud computing platform.

10. The method according to claim 1, wherein said remote computing server is a standalone server for individual task and a cloud server for large scale tasks and enabled with GPU.

* * * * *